(12) United States Patent
Baker et al.

(10) Patent No.: US 12,142,383 B2
(45) Date of Patent: *Nov. 12, 2024

(54) GEO-CLUSTERING FOR DATA DE-IDENTIFICATION

(71) Applicant: PRIVACY ANALYTICS INC., Ottawa (CA)

(72) Inventors: Andrew Richard Baker, Alcove (CA); Khaled El Emam, Ottawa (CA)

(73) Assignee: Privacy Analytics Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/828,073

(22) Filed: May 31, 2022

(65) Prior Publication Data

US 2022/0293280 A1    Sep. 15, 2022

Related U.S. Application Data

(62) Division of application No. 15/591,630, filed on May 10, 2017, now Pat. No. 11,380,441.

(60) Provisional application No. 62/334,261, filed on May 10, 2016.

(51) Int. Cl.
| | |
|---|---|
| G16H 50/30 | (2018.01) |
| G06F 16/29 | (2019.01) |
| G16H 10/60 | (2018.01) |
| H04L 67/52 | (2022.01) |

(52) U.S. Cl.
CPC .......... *G16H 50/30* (2018.01); *G06F 16/29* (2019.01); *H04L 67/52* (2022.05); *G16H 10/60* (2018.01)

(58) Field of Classification Search
None
See application file for complete search history.

(56) References Cited

U.S. PATENT DOCUMENTS

| | | | |
|---|---|---|---|
| 8,676,799 B1 | 3/2014 | Vaver | |
| 2002/0169793 A1* | 11/2002 | Sweeney | G06Q 20/383 715/255 |
| 2004/0117448 A1* | 6/2004 | Newman | G06F 16/353 707/E17.09 |
| 2011/0040797 A1 | 2/2011 | Haskell | |
| 2011/0258206 A1 | 10/2011 | El Emam | |

(Continued)

OTHER PUBLICATIONS

El Emam, Khaled, and Fida Kamal Dankar. "Protecting privacy using k-anonymity." Journal of the American Medical Informatics Association 15.5 (2008): 627-637. (Year: 2008).*

(Continued)

*Primary Examiner* — Alex Gofman
*Assistant Examiner* — Umar Mian
(74) *Attorney, Agent, or Firm* — ALG Intellectual Property, LLC

(57) ABSTRACT

Methods and systems to de-identify data records, including to merge pairs of clusters data records of individuals until a number of data records of each cluster meets a minimum size threshold, de-identify the clusters when each cluster meets the minimum size threshold, assess a risk of re-identification of the de-identified clusters based on k-anonymity, increase the minimum size threshold and re-perform the merge, the de-identify, and the assess a risk, if the assessed risk does not meet a risk criterion, and present the de-identified clusters on a display when the assessed risk meets the risk criterion.

19 Claims, 6 Drawing Sheets

(56) References Cited

U.S. PATENT DOCUMENTS

| | | | |
|---|---|---|---|
| 2011/0321169 A1* | 12/2011 | Cormode | G06F 21/6254 |
| | | | 726/26 |
| 2013/0238625 A1 | 9/2013 | Binkowski | |
| 2015/0169976 A1 | 6/2015 | Ibrahim | |
| 2015/0326461 A1* | 11/2015 | Singh | H04L 43/12 |
| | | | 709/224 |

OTHER PUBLICATIONS

El Emam, Khaled, et al. "A Globally Optimal k-Anonymity Method for the De-Identification of Health Data." J Am Med Inform Assoc 16 (2009): 670-682. (Year: 2009).*

* cited by examiner

GEO-CLUSTERING FOR DATA DE-IDENTIFICATION

CROSS-REFERENCE TO RELATED APPLICATIONS

This application is a divisional of U.S. Ser. No. 15/591,630, filed May 10, 2017, entitled, "GEO-CLUSTERING FOR DATA DE-IDENTIFICATION", which claims the benefit of U.S. Provisional Application Ser. No. 62/334,261, filed on May 10, 2016, both of which are hereby incorporated by reference in their entirety.

TECHNICAL FIELD

The present disclosure relates to data de-identification and in particular to geo-clustering data for de-identification.

BACKGROUND

When health records are reused for secondary purposes, the geographic location of patients often has analytic utility, but precise locations can be too identifying. The current method of generalizing geocodes, such as ZIP code or other postal codes (collectively referred to a geocodes), is to truncate the code, grouping multiple regions with the same prefix. However, these codes are assigned for the purposes of facilitating mail delivery, not with other secondary purposes in mind, and as such, clusters created by this method have many undesirable properties.

Basic ZIP codes are given by a five-digit numeric sequence. The first digit of a ZIP code identifies a set of states. For example, ZIP codes starting with 7 may fall within multiple states. The next two digits represent the Sectional Center Facility (SCF). This is a facility which processes and distributes mail to the local post offices. The final two digits indicate the town or section of a city. (In 1989 ZIP codes were extended to the ZIP+4 system which further specifies the location within the ZIP code. However, this additional information typically is too identifiable so only the first 5 digits are considered.)

Canadian postal codes have a similar structure; however they are represented by a six-digit sequence of alternating letters and numbers. The first digit indicates the postal district, typically a whole province or territory, though Ontario and Quebec have multiple postal districts. The first three digits together indicate the forward sort area (FSA). (If the second character is zero, it indicates a rural area; non-zero second characters indicate an urban area.) The last three characters indicate the local delivery unit (LDU).

Other geographic regions include, but are not limited to, those created for the purposes of administering a census or providing services, e.g., education or health care services, or to denote a demographic such as an income group or cost of living group. Individual points may not be associated with a strictly delimited area, but serve a surrounding region such as cell phone towers or franchise locations. Such sets of regions or points may or may not have a pre-existing grouping or generalization scheme. This scheme applies to both regions and points, whether or not there is pre-existing grouping.

The concept of k-anonymity often is used when de-identifying health datasets. This requires that every individual in a dataset looks like at least k−1 other individuals. The purpose of generalizing geocodes is to increase the number of individuals in each geocluster so that matching individuals are more likely to be found. For example, there may be one male born in 1970 living in ZIP code 12451 but three males born in 1970 living in ZIP code 12452. If the ZIP code is generalized to four digits, then there are at least four males born in 1970 living in 1245x.

Present truncation clustering schemes provide only limited options for generalization. The first digit of a ZIP code typically is common to the entire state, and even the first two digits provide little, if any, delineation within state boundaries. Going to four or five digits provides greater specificity, but often is too identifying.

Accordingly, systems and methods that enable improved de-identification of geocoding remain highly desirable.

SUMMARY

This specification outlines a new approach of pre-calculating a more appropriate hierarchy of geocoded clusters which will allow the quality of the de-identified dataset to increase and provide greater granularity to the generalization levels.

A new clustering method is provided specifically designed to meet the needs of clustering geocodes for the purposes of achieving k-anonymity. In comparison to the traditional geocode truncation scheme and clustering methods based on space filling curves, the descried method distorts the data to a lesser extent while also avoiding undesirable properties inherent in the other approaches.

A three-digit crop (i.e., a prefix) often is used for both ZIP codes and other postal codes corresponding with the regional mail processing stations, though other prefix lengths will provide greater or less generalization of the geographic region. However, even with the standard three-digit crop, there are a variety of problems which arise.

Embodiments of the present invention are directed to a method of geo-clustering for data de-identification of a dataset from a data source. The method includes retrieving, by a server, a dataset including a plurality of geocodes, wherein each geocode is associated with an area having a population or a point servicing a surrounding region. Further, the server determines a plurality of geoclusters based on the plurality of geocodes, wherein each of the plurality of geocodes is initialized as a corresponding geocluster. The method further comprises identifying, by the server, a geocluster among the plurality of geoclusters having the smallest population; setting, by the server a first geocluster as the geocluster having the smallest population; identifying a second geocluster wherein the second geocluster is a geocluster among the plurality of geoclusters that is nearest to the first geocluster; and iteratively merging the first geocluster and the second geocluster until a minimum population threshold is met.

Other embodiments are directed to a system for geo-clustering for de-identification of a dataset from a data source. The system comprises an input/output interface configured to receive a dataset, including a plurality of geocodes, from the data source, wherein each geocode is associated with a population, and a server communicably coupled to the input/output interface. The server is configured to determine the plurality of geoclusters based on the dataset, wherein each of the plurality of geocodes is initialized as a corresponding geocluster, identify a geocluster among the plurality of geoclusters with the smallest population, set a first geocluster as the geocluster having the smallest population, identify a second geocluster, wherein the second geocluster is a geocluster among the plurality of geoclusters that is nearest to the first geocluster and iteratively merge the first geocluster with the second geocluster until a minimum population threshold is met.

Yet other embodiments are directed to a method of geo-clustering for data de-identification of a dataset from a data source. The method comprises retrieving, by an input interface, risk assessment metrics for de-identification; determining, by a server, a minimum population threshold based on the risk assessment metrics, wherein the server is coupled communicatively to the input interface; retrieving, by a server, a dataset including a plurality of geocodes, wherein each geocode is associated with an area having a population; determining, by the server, a plurality of geoclusters based on the plurality of geocodes, wherein each of the plurality of geocodes is initialized as a corresponding geocluster, identifying, by the server, a geocluster among the plurality of geoclusters with the smallest population; identifying, by the server, a second geocluster, wherein the second geocluster is a geocluster among the plurality of geoclusters that is nearest to the first geocluster; and iteratively merging the first geocluster and the second geocluster until a minimum population threshold is met. The server performs de-identification of the dataset pertaining to the first geocluster which has the smallest population greater than the minimum population threshold and stores the de-identified dataset in a memory.

The system described herein is illustrated with relation to de-identifying datasets under a risk measurement or risk assessment model of k-anonymity, but the system can be similarly applied to other risk measurement models.

BRIEF DESCRIPTION OF THE DRAWINGS

Further features and advantages of the present invention will become apparent from the following detailed description, taken in combination with the appended drawings, in which.

Figure 1:
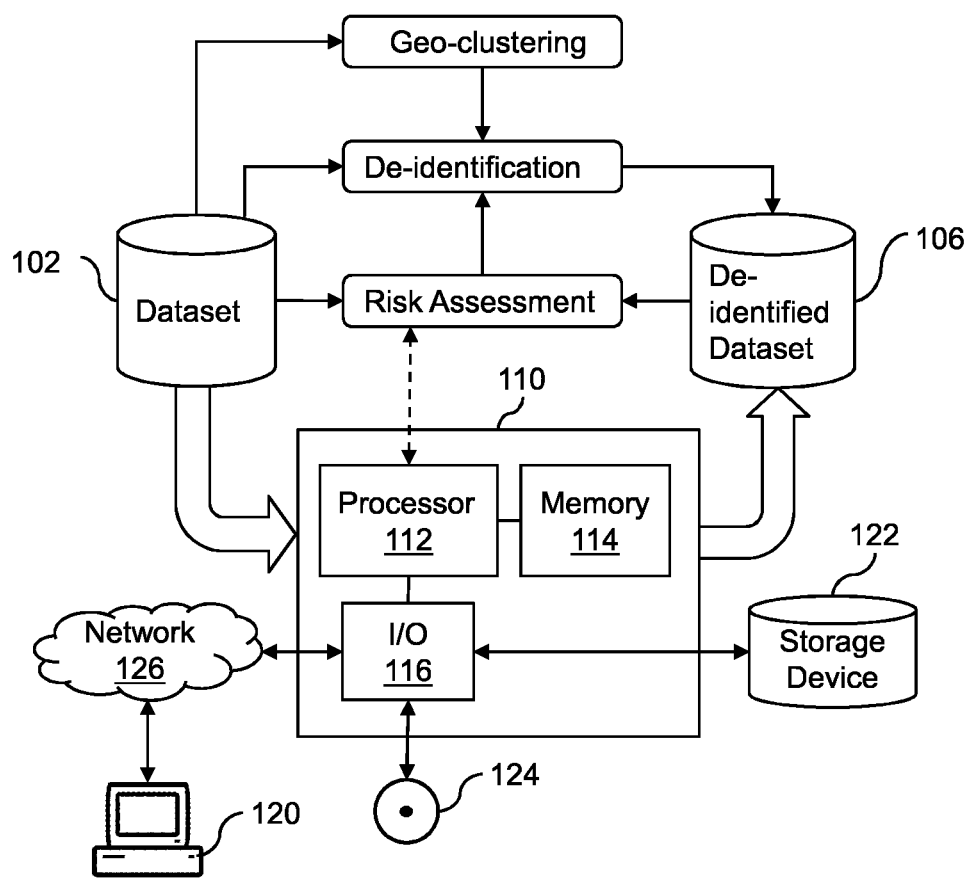
FIG. 1 shows a system of geo-clustering for data de-identification, according to an aspect of the disclosure.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

It will be noted that throughout the appended drawings, like features are identified by like reference numerals.

DETAILED DESCRIPTION

Embodiments of the present disclosure will be described below in conjunction with exemplary systems and methods for geo-clustering data and de-identification of a dataset. In the present disclosure, geoclusters may be interchangeably referred to as clusters.

Embodiments of the present disclosure are directed to a method of geo-clustering of data for de-identification of a dataset. The method includes generating a plurality of geoclusters based on a plurality of geocodes. The geocodes may include ZIP codes or other postal codes. The method further includes identifying the geoclusters having the smallest population. The geocluster having the smallest population is merged iteratively with the nearest geoclusters until a minimum population threshold is met. Once the smallest geocluster meets the minimum population threshold, a corresponding dataset is de-identified.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. The terms "comprising", "including", and "having" may be used interchangeably.

Embodiments are described below, by way of example only, with reference to FIGS. 1-6.

FIG. 1 provides a system 100 for risk measurement and suppression for de-identification of a dataset using geo-clustering in connection with the above described method. A computer or server 110 includes at least one processor 112, a memory 114 and an input/output interface 116. In an embodiment, the server 110 implements the code for executing the de-identification process. A dataset 102 from a data source is stored on a computer readable storage memory which may reside locally or remotely from the processor 112. The dataset 102 is processed by the server 110 to provide risk assessment which can be used for optimal de-identification. Generalization strategies and levels of suppression also may be provided through template files, user selection or input through interaction with the server 110, either directly through input devices such as, a keyboard/mouse and a display 120 or remotely through a connected computing network 126.

The network 126 may include a data network such as, but not restricted to, the Internet, local area network (LAN), wide area network (WAN), metropolitan area network (MAN), etc. In certain embodiments, the network 126 can include a wireless network, such as, but not restricted to, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS) etc. In some embodiments, the network 126 may include or otherwise cover networks or subnetworks, each of which may include, for example, a wired or wireless data pathway. The network 126 may include a circuit-switched voice network, a packet-switched data network, or any other network capable for carrying electronic communications. For example, the network 126 may include networks based on the Internet protocol (IP) or asynchronous transfer mode (ATM), and may support voice usage, for example, Voice-over-IP (VoIP), Voice-over-ATM, or other comparable protocols used for voice data communications. In one implementation, the network 126 includes a cellular telephone network configured to enable exchange of text or SMS messages.

Examples of the network 126 may further include, but are not limited to, a personal area network (PAN), a storage area network (SAN), a home area network (HAN), a campus area network (CAN), a local area network (LAN), a wide area network (WAN), a metropolitan area network (MAN), a virtual private network (VPN), an enterprise private network (EPN), Internet, a global area network (GAN), and so forth.

An external storage 122, or computer readable memory, such as a compact disc, a digital versatile disc or other removable memory devices 124 may be used to provide the instructions for execution of the risk assessment and de-identification methods or provide input for generalization or suppression parameters via the input/output interface 116. Execution of the method on the processor 112 retrieves a de-identified dataset 106 and provides an assessment of risk or provide the resulting parameters which can be utilized in performing geo-clustering to optimize de-identification of the dataset to meet a desired risk threshold. The de-identification process may use optimization such as optimal lattice anonymization for determining a level of de-identification which meets a desired risk threshold. In an embodiment, the system 100 may display the de-identified dataset on the display 120 after performing de-identification.

In an embodiment, the system 100 receives the dataset 102 which includes multiple geocodes such as, ZIP codes or other postal codes. In some embodiments, the ZIP codes may be truncated at varying lengths. For example, the dataset 102 may include quasi-identifiers, such as ZIP codes that are truncated at a ZIP-4 truncation, and ZIP codes that are truncated at a ZIP-3 truncation.

Figure 2:
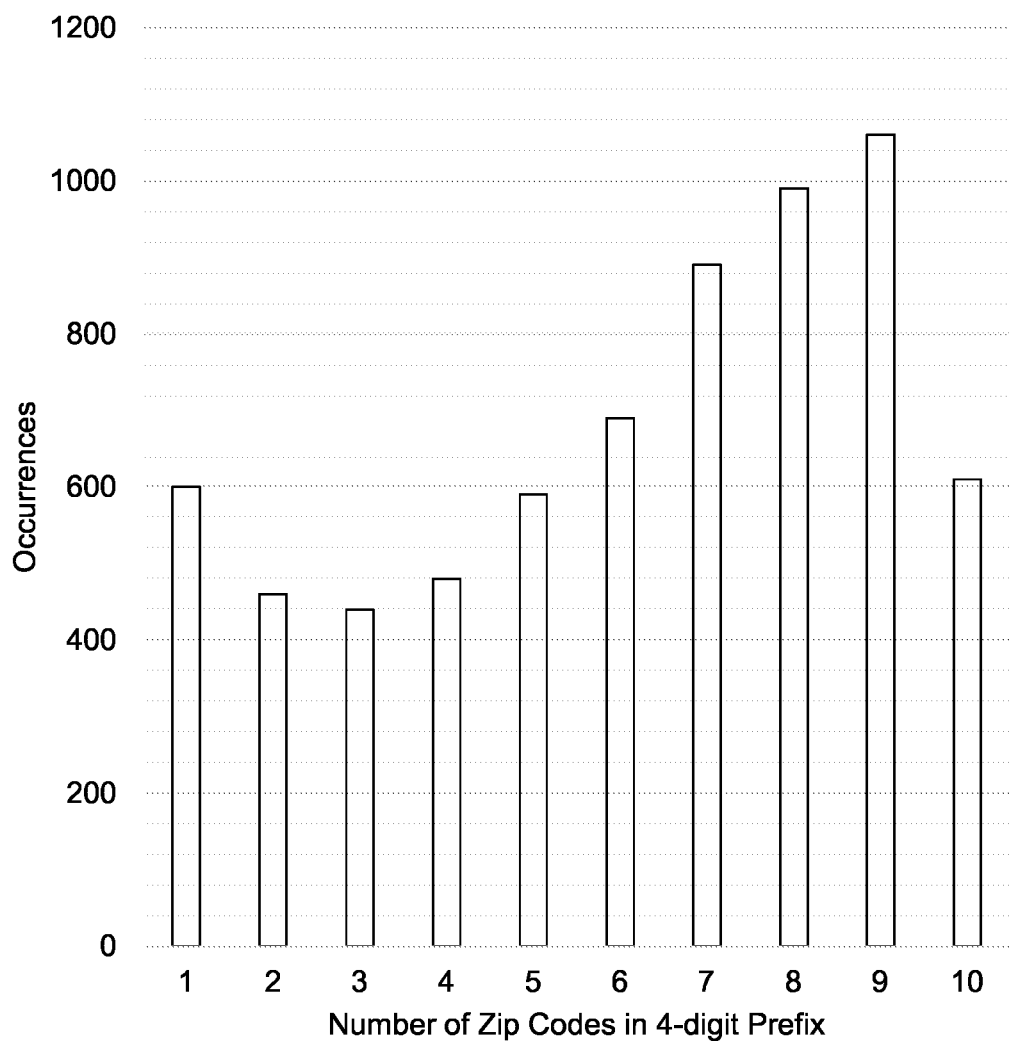
FIG. 2 shows a graph of a representation of distribution of cluster sizes under a ZIP-4 truncation.
Figure 3:
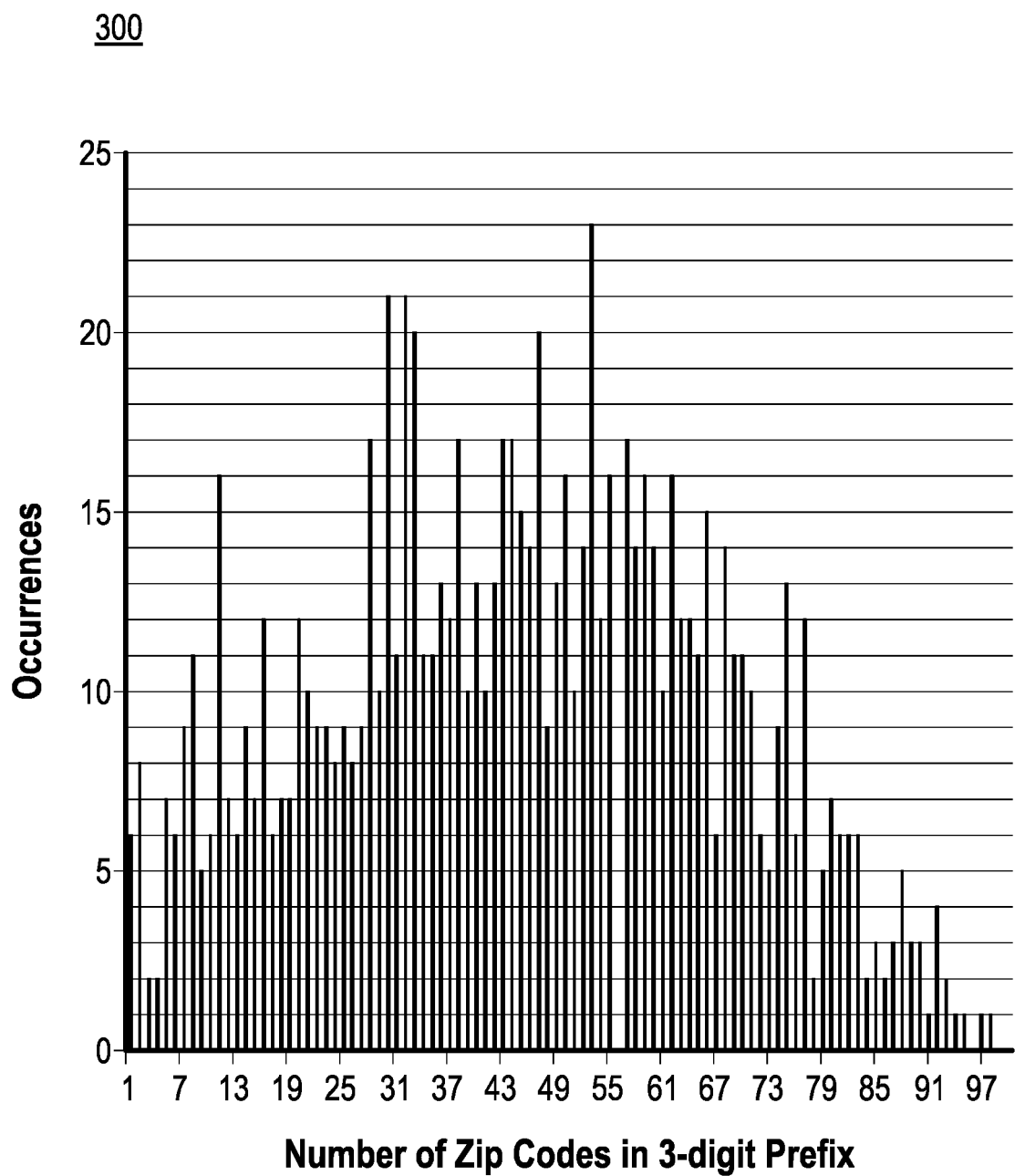
FIG. 3 shows a graph of a representation of distribution of cluster sizes under a ZIP-3 truncation.

Exemplary source data, as illustrated in FIGS. 2 and 3, includes ZIP code data geocoded by an external data source which provides centroid latitude and longitude values for each zip code, and the ZIP code tabulation area (ZCTA) records which contain population counts and areas for each ZCTA region (which generally correspond to ZIP codes).

In an embodiment, the system 100 performs geo-clustering based on truncated ZIP codes obtained from the data source. The system 100 initializes a geocluster with a ZIP code. Each geocluster is initiated as an individual geocoded region with the original centroid, area, and population. The population-based clusters described herein allow for additional levels of generalization, resulting in improved control over the de-identification process.

In an embodiment, the system 100 utilizes a two-fold greedy process to preferentially merge geoclusters which have a small population. Taking a minimum population size as a parameter, clusters are merged until the cluster with the smallest population satisfies a minimum size. Specifically, the system 100 identifies the geocluster with the smallest population, and performs clustering until the smallest population satisfies a minimum population threshold or no further merging is possible. The minimum population threshold is determined based on risk assessment criteria for de-identifying the dataset 102. In an embodiment, risk assessment criteria include k-anonymity.

In an embodiment, the system 100 merges the minimum population geocluster with its nearest geocluster. In a further embodiment, the dataset 102 is searched for the cluster which is the closest based on the distance metrics such as the Hausdorff distance or road distance. The two clusters are merged into a single resulting cluster. The centroid latitude and longitude of the new cluster are calculated. The resulting population and area are a function of the respective values in the two clusters. In some embodiments, the function may be a summation (of population) or concatenation (of area). In other embodiments, if there are fuzzy boundaries between regions, the resulting population or area may be based upon a function other than strictly a sum of the two populations or a concatenation of the two areas.

In an embodiment, the system 100 may optionally create a hierarchy of geoclusters. Creating a hierarchy of geoclusters is tied closely to the process of performing an optimal k-anonymous de-identification on a dataset. To obtain a k-anonymous dataset, values must be generalized and/or suppressed in order to ensure that each individual in the dataset looks like at least k−1 other individuals in the dataset according to the quasi-identifier values. The properties of the dataset may determine the amount of generalization which is required. A sparse distribution of values within a quasi-identifier or large number of quasi-identifiers will generally require greater generalization than a dataset with a dense distribution across few quasi-identifiers.

In an embodiment, a hierarchy of geoclusters may include geoclusters in a hierarchy based on a level of truncation of ZIP codes. For example, the hierarchy includes a first set of geoclusters associated with the ZIP code 12345 and a second set of geoclusters associated with the ZIP code 1234x. The second set of geoclusters is placed hierarchically above the first set of geoclusters. In another embodiment, a hierarchy of geoclusters may include geoclusters in a hierarchy based on geographic location. For example, geoclusters pertaining to a state may be placed above geoclusters pertaining to a city in the hierarchy. Further, the hierarchy may be based on a combination of the level of truncation of ZIP/postal codes and level of geographic division (e.g., state, county etc.).

Such additional processing, such as creation of a hierarchy of geoclusters, may not increase the complexity of the de-identification process as the hierarchy of clusters may be used with an Optimal Lattice Anonymization (OLA) process to automatically choose a generalization scheme which results in a k-anonymous dataset with only a small amount of suppression.

Since the geoclusters are based on population size, the situation is avoided of having some clusters that are highly populated while other clusters are sparsely populated. Assuming that the individuals in the dataset are evenly distributed across the geographic regions, a situation where some equivalence classes (groups of individuals who look alike) are very large while others are extremely small than with the truncation cluster scheme is less likely to be encountered. Thus, an overall level of data manipulation required to reach k-anonymity will be lower than with the truncation clustering scheme.

By constraining the way the geoclusters grow, with population-based geoclusters individuals remain closer to their true location after the generalization process compared to under truncation. Besides the geographic distance, additional criteria can be placed upon the selection of the nearest geocluster. Hard constraints can be imposed to restrict the selection of the nearest geocluster to a subset of all geoclusters. This can be used to force geoclusters to respect boundaries such as political jurisdictions. Soft constraints can be imposed to preferentially select a nearest geocluster which is similar in terms of socioeconomic, demographic, political and/or other characteristics over the region which is closest based strictly on the geographic distance. As these constraints can be realized as an additional factor in the distance calculations, the following refers to the nearest region but may also include such hard or soft constraints. This can improve the value of analyses performed on the de-identified dataset.

In an embodiment, the following pseudocode illustrates merging of clusters:
initialize each geocode as its own geocluster
order geoclusters by population
SmallestCluster:=cluster with minimum population
while population(SmallestCluster)<threshold
    NearestCluster:=cluster closest to SmallestCluster (!=SmallestCluster)
    merge SmallestCluster with NearestCluster
    update Latitude, Longitude, Area, and Population of NearestCluster
    SmallestCluster:=cluster with minimum population In another embodiment, the system 100 may execute the aforementioned method multiple times with different minimum population thresholds. This creates cluster sets with different levels of generalization. In order to de-identify a highly-identifying dataset, the location may need to be generalized to a larger region than is required for a dataset which has few identifying features. This is already accomplished by truncating ZIP codes or other postal codes to different lengths, but the greedy population approach creates more levels in the hierarchy to provide greater granularity in the generalization process.

A hierarchy created by this method is guaranteed to satisfy the nesting property. This means that a cluster is always a subset of a cluster at a higher level of generalization. This is a desirable or necessary property for some generalization processes.

Examples of dataset that are retrieved by the system 100 from a data source for geo-clustering are described with reference to FIGS. 2 and 3.

FIG. 2 illustrates a graph 200 with a distribution of cluster sizes under a 4-digit ZIP code truncation. The number of clusters varies across various ZIP codes as can be seen from the varying number of occurrences against a number of ZIP codes corresponding to a 4-digit prefix. The assumption of any truncation generalization scheme is that shortening the prefix of a ZIP code will result in more clusters being merged together. However, this happens unevenly across the data set. For example, a geocluster given by ZIP prefix 1234x, may have only a single code in this cluster. Conversely, for a ZIP prefix 1245x, there may be ten codes clustered.

When extended to 3-digit ZIP code truncation, a wide range of cluster sizes are still present as shown on the graph 300 in FIG. 3. With a 3-digit ZIP code truncation, it can be seen that merging of codes is more uneven in this truncation scheme. This means that even when truncating to 3 digits there are some clusters which only contain a single code or a handful of codes, while others group almost 100 codes together.

In an embodiment, the system 100 may use the truncated ZIP codes of FIGS. 2 and 3 to generate geoclusters. Both ZIP codes and other postal codes correspond to wildly differing population sizes, as do various levels of clustering, resulting in different shapes and sizes of regions.

Some regions may be long and strung out, possibly due to the region following a major highway, or the region lying between two geographic features. These regions bear a similarity to chili peppers (and coincidently the country Chile) and gerrymandered political districts (i.e., convoluted districts created for political gain).

In many cases, the core of a city receives a different sectional center facility (SCF) code than the surrounding suburbs. This is referred to as a donut, based on the shape of the suburb cluster. Other cities may come close to being surrounded by a donut, but do not because they may border a large water body.

In some cases, a cluster is broken into separate pieces which are not connected to each other. Along with donuts, these shapes are undesirable from an analytical point of view.

Some geocode prefixes serve the same area. For example, there are regions that each are served by two different Sectional Center Facility (SCF) codes but which largely cover the same geographic area or have significant overlap.

There are some regions which receive anomalous codes for the purpose of facilitating mail delivery. For example, every ZIP code in a state may begin with 1xxxx, except for an island within that state, which may have the ZIP code beginning 0xxxx. This is because the only ferry to the island originates in another state, and as such the mail for the island is routed through that state. In another example, ZIP codes in a state may all start with a 7xxxx. However, there may be one section of that state where the mail is routed through a neighboring state so these regions have a ZIP prefix of 885xx.

The system 100 (shown in FIG. 1) may use datasets illustrated in FIGS. 2 and 3 to generate high quality clusters. Such high quality clusters may enhance de-identification on the resulting data. The quality of the de-identified dataset means that there is less generalization and suppression, and that the perturbation of the data is less than under a truncation scheme, such as 4-digit ZIP and/or 3-digit ZIP truncation schemes. The system 100 also may establish a baseline to measure the cluster quality, the suppression and the entropy of the de-identified dataset when running the existing truncation-based geo-clustering methods.

In an embodiment, cluster quality is measured using the Davies-Bouldin index and/or the Dunn index. The system 100 may use such evaluation metrics to measure the quality of a clustering scheme. The Hausdorff distance is used to measure the distance between two clusters when the system 100 generates clusters and evaluates their quality. This takes into account the curvature of the Earth and the size of the two clusters. To measure the impact on the de-identified dataset, the number of data elements missing relative to the data in the original dataset and the entropy of the final dataset, is found.

Figure 4:
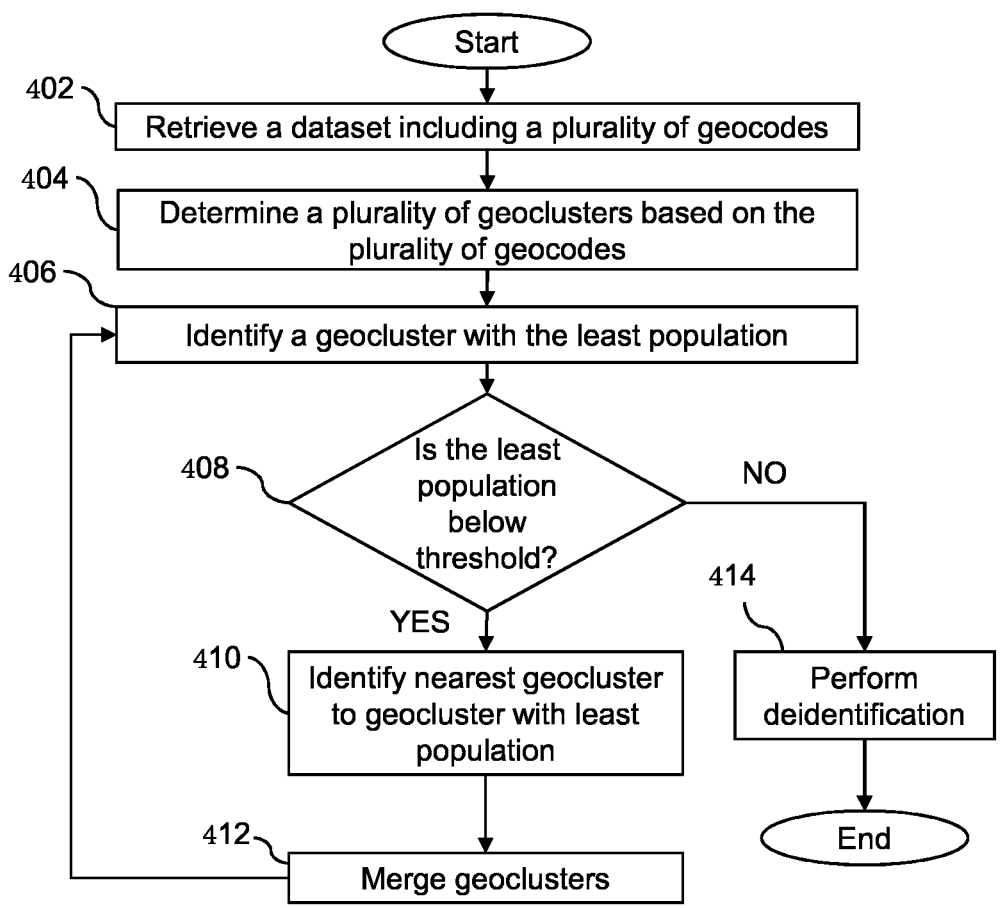
FIG. 4 shows a method of geo-clustering for data de-identification, according to an aspect of the disclosure.

FIG. 4 illustrates a method 400 of geo-clustering data for de-identifying the dataset 102 from a data source. The method 400 may be implemented using the system 100 of FIG. 1. The dataset 102 includes data pertaining to people living in a region and quasi-identifiers such as geocodes. Geocodes may include ZIP codes, other postal codes, truncated forms of these geocodes, or other values which can be mapped to a specific geographic location, and are associated with areas having a population. For example, the dataset 102 may include information relating to the medical files of people associated with a health insurance company, living at addresses with ZIP code 1245x. The ZIP code 1245x is a quasi-identifier for the medical files of these people.

At step 402, the dataset 102 is retrieved from an external data source. The dataset 102 may be stored on the server 110 or in an external memory. At step 404, a plurality of geoclusters are determined from the dataset 102. Each of the plurality of geocodes is initialized as a corresponding geocluster. In some embodiments, the plurality of geoclusters are of different generalizations based on truncation lengths of the corresponding ZIP codes or other postal codes.

In some embodiments, a generalization strategy is selected to meet an optimal lattice anonymization such that k-anonymity is satisfied and information loss is minimized. The hierarchy of clusters may be used with an Optimal Lattice Anonymization (OLA) process to automatically choose a generalization scheme which results in a k-anonymous dataset with only a small amount of suppression.

The hierarchy of the plurality of geoclusters may be further based on requirements of k-anonymity de-identification of the dataset. The quality of the geoclusters is measured using the Davies-Bouldin index and the Dunn index. Further the Hausdorff distance is used to measure the distance between two geoclusters.

At step 406, a geocluster with the smallest population among the plurality of geoclusters, is identified. The server 110 sets a first geocluster as the geocluster having the smallest population.

At step 408, the smallest population is determined to be higher or lower than a minimum population threshold. The minimum population threshold is determined based on risk assessment criteria for de-identifying the dataset 102. Risk assessment criteria include k-anonymity. If the smallest population is determined to be lesser than the threshold, at step 410, a second geocluster, that is the nearest in distance from the first geocluster is identified and merged with the second geocluster. In some embodiments, the second geocluster is further identified through external constraints that are provided to the clustering method, ensuring that regions which are clustered are alike according to additional properties. External constraints include socio-economic, demographic and/or political parameters. For example, with reference to de-identifying a patient database of a hospital, the nearest geocluster to an identified first geocluster may be outside the purview of the hospital due to factors such as demographics, political issues or socio-economics. The hospital may cater to patients of only a specific category which may not include the area covered by the closest geocluster. In such instances, the server 110 identifies the next nearest geocluster as the second geocluster.

At step 412, the first and second geoclusters are merged. Accordingly, centroid latitude, centroid longitude, area and population of the merged geocluster are calculated. The resulting population and area are the sum of the respective values of the first and second geoclusters. Steps 406 to 412 are repeated until a geocluster having the smallest population is determined to have a population greater than the minimum population threshold is identified. Alternatively, if the first geocluster is determined to have a population greater than the minimum population threshold, then at step 414, the dataset can immediately be de-identified by the server 110.

Figure 5:
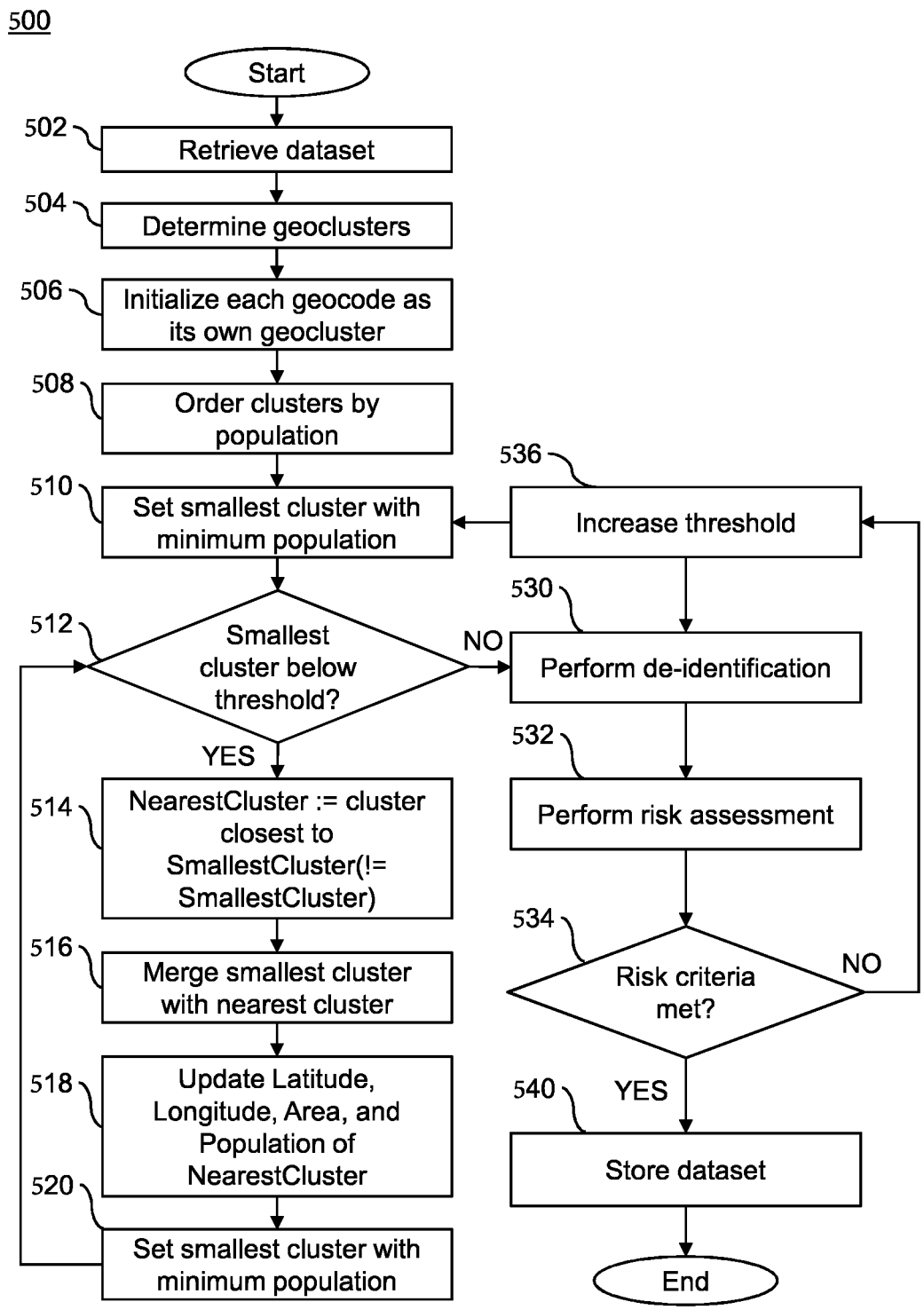
FIG. 5 shows a method of geo-clustering for data de-identification, according to an aspect of the invention.

FIG. 5 illustrates a method 500 of geo-clustering data for execution by the server 110 (shown in FIG. 1). At step 502, the dataset 102 is retrieved from a storage device either coupled to the server 110 or remotely accessible. Geoclusters are determined for the dataset 102 at step 504. Each geocode is initialized by its own geocluster at step 506. The clusters are then ordered by population at step 508. The smallest cluster is set to be the cluster with the smallest population at step 510. Based upon the de-identification requirements a threshold is set for the population number required in the cluster to achieve de-identification requirements. If the smallest cluster is below the threshold (YES at step 512) the server 110 proceeds to step 514 in which the closest cluster to the smallest cluster is set as the nearest cluster. The smallest cluster is then merged with the nearest cluster at step 516. The Latitude, Longitude, Area, and Population of NearestCluster is updated to include the smallest cluster information at step 518. At step 520, the smallest cluster is then set to the new smallest cluster. The process is performed until the smallest cluster is larger than the threshold (NO at step 512). De-identification is performed at step 530 and risk assessment of the de-identified dataset is performed at step 532. If risk criteria, such as k-anonymity is met (YES at step 534), then step 540 stores the dataset in a memory, e.g., a removable memory. If the risk criteria are not met (NO at step 534) the population size threshold is increased, which is implemented at step 536.

Figure 6:
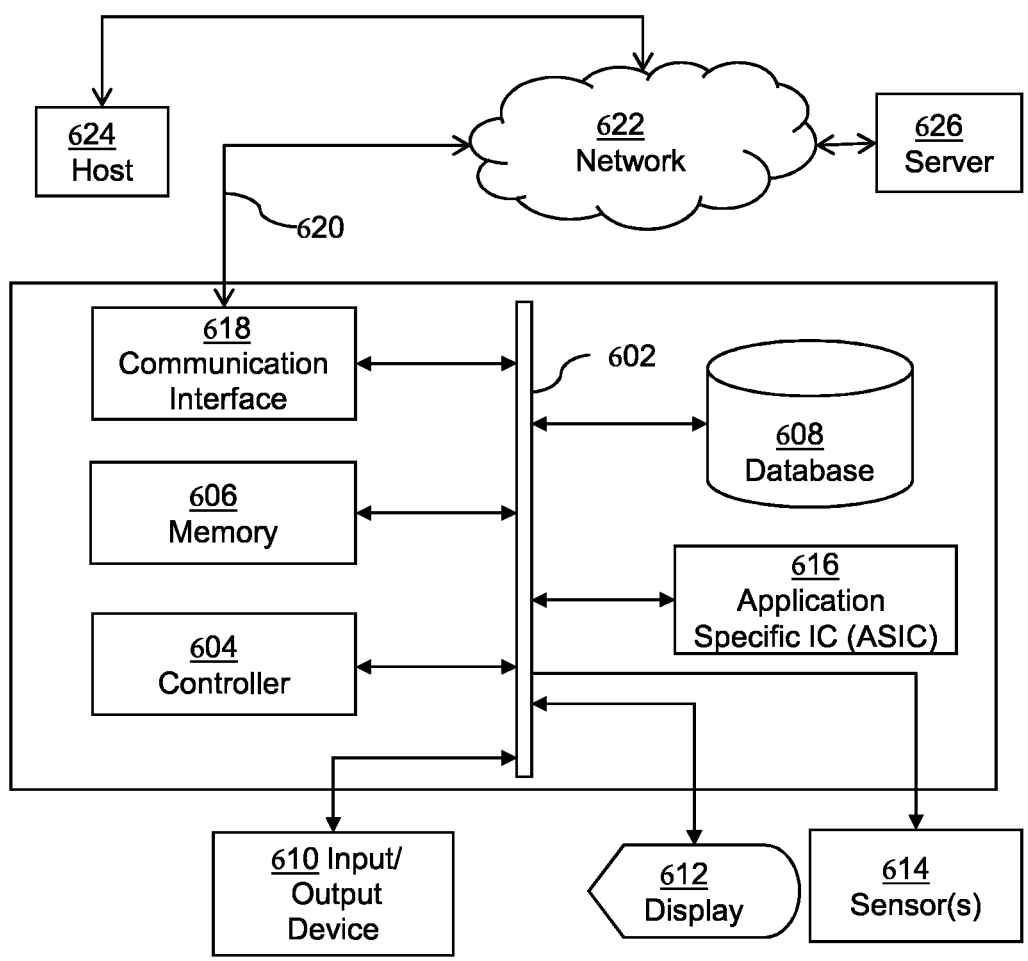
FIG. 6 is a computer system that can be used to implement various exemplary embodiments of the disclosed subject matter While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the particular form disclosed, but to the contrary, the present disclosure is to cover all modification, equivalents and alternatives falling within the spirit and scope of embodiments of the present disclosure as defined by the appended claims.

FIG. 6 illustrates a computer system 600 upon which the operation of the server 110 may be implemented. Although, the computer system 600 is depicted with respect to a particular device or equipment, it is contemplated that other devices or equipment (e.g., network elements, servers, etc.) within FIG. 6 can deploy the illustrated hardware and components of system. The computer system 600 is programmed (e.g., via computer program code or instructions) to retrieve the dataset 102 from an external data source and includes a communication mechanism such as a bus 602 for passing information between other internal and external components of the computer system 600. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. The computer system 600, or a portion thereof, constitutes a means for performing one or more steps retrieving data from the data source.

A bus 602 includes one or more parallel conductors of information so that information is transferred quickly among devices coupled to the bus 602. A processor 604 for processing information are coupled with the bus 602.

The processor 604 performs a set of operations on information as specified by an end-user. The computer program code is a set of instructions or statements providing instructions for the operation of the processor 604 and/or the computer system 600 to perform specified functions. The code, for example, may be written in a computer programming language that is compiled into a native instruction set of the processor 604. The code also may be written directly using the native instruction set (e.g., machine language). The set of operations include bringing information in from the bus 602 and placing information on the bus 602. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 604, such as a sequence of operation codes, constitute processor instructions, also called computer system instructions or, simply, computer instructions. The processor 604 may be implemented as mechanical, electrical, magnetic, optical, chemical, or quantum components, among others, alone or in combination.

The computer system 600 also includes a memory 606 coupled to the bus 602. The memory 606, such as a Random Access Memory (RAM) or any other dynamic storage device, stores information including processor instructions for storing information and instructions to be executed by the processor 604. The dynamic memory 606 allows information stored therein to be changed by the computer system 600. RAM allows a unit of information stored at a location called a memory address to be stored and retrieved independently of information at neighboring addresses. The memory 606 is also used by the processor 604 to store temporary values during execution of processor instructions. The computer system 600 also includes a Read Only Memory (ROM) or any other static storage device coupled to the bus 602 for storing static information, including instructions, that is not changed by the computer system 600. Some memory is composed of volatile storage that loses the information stored thereon when power is lost. Also coupled to the bus 602 is a non-volatile (i.e., persistent) storage device 608, such as a magnetic disk, a solid state disk, optical disk or flash card, for storing information, including instructions, that persists even when the computer system 600 is turned off or otherwise loses power.

Information is provided to the bus 602 for use by the processor 604 from an external input device 610, such as a keyboard containing alphanumeric keys operated by a human user, a microphone, an Infrared (IR) remote control, a joystick, a game pad, a stylus pen, a touch screen, or a sensor. The sensor detects conditions in its vicinity and transforms those detections into physical expression compatible with the measurable phenomenon used to represent information in the computer system 600. Other external devices coupled to the bus 602, used primarily for interacting with humans, include a display 612, such as a Cathode Ray Tube (CRT), a Liquid Crystal Display (LCD), a Light Emitting Diode (LED) display, an organic LED (OLED) display, active matrix display, Electrophoretic Display (EPD), a plasma screen, or a printer for presenting text or images, and a pointing device, such as a mouse, a trackball, cursor direction keys, or a motion sensor, for controlling a position of a small cursor image presented on the display 612 and issuing commands associated with graphical elements presented on the display 612, and one or more camera sensors 614 for capturing, recording and causing to store one or more still and/or moving images (e.g., videos, movies, etc.) which also may comprise audio recordings. Further, the display 612 may be a touch enabled display such as capacitive or resistive screen. In some embodiments, for example, in embodiments in which the computer system 600 performs all functions automatically without human input, one or more of the external input device 610, and the display 612 may be omitted.

In the illustrated embodiment, special purpose hardware, such as an ASIC 616, is coupled to the bus 602. The special purpose hardware is configured to perform operations not performed by the processor 604 quickly enough for special purposes. Examples of ASICs include graphics accelerator cards for generating images for the display 612, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

The computer system 600 also includes one or more instances of a communication interface 618 coupled to the bus 602. The communication interface 618 provides a one-way or two-way communication coupling to a variety of external devices that operate with their own processors, such as printers, scanners and external disks. In general, the coupling is with a network link 620 that is connected to a local network 622 to which a variety of external devices with their own processors are connected. For example, the communication interface 618 may be a parallel port or a serial port or a Universal Serial Bus (USB) port on a personal computer. In some embodiments, the communication interface 618 is an Integrated Services Digital Network (ISDN) card, a Digital Subscriber Line (DSL) card, or a telephone modem that provides an information communication connection to a corresponding type of a telephone line. In some embodiments, the communication interface 618 is a cable modem that converts signals on the bus 602 into signals for a communication connection over a coaxial cable or into optical signals for a communication connection over a fiber optic cable. As another example, the communication interface 618 may be a Local Area Network (LAN) card to provide a data communication connection to a compatible LAN, such as Ethernet™ or an Asynchronous Transfer Mode (ATM) network. In one embodiment, wireless links also may be implemented. For wireless links, the communication interface 618 sends or receives or both sends and receives electrical, acoustic or electromagnetic signals, including infra-red and optical signals that carry information streams, such as digital data. For example, in wireless handheld devices, such as mobile telephones like cell phones, the communication interface 618 includes a radio band electromagnetic transmitter and receiver called a radio transceiver. In certain embodiments, the communication interface 618 enables connection to the network 126 for inspecting the user queries. Further, the communication interface 618 can include peripheral interface devices, such as a thunderbolt interface, a Personal Computer Memory Card International Association (PCMCIA) interface, etc. Although a single communication interface 618 is depicted, multiple communication interfaces also may be employed.

The term "computer-readable medium" as used herein refers to any medium that participates in providing information to the processor 604, including instructions for execution. Such a medium may take many forms, including, but not limited to, computer-readable storage medium (e.g., non-volatile media, volatile media), and transmission media. Non-transitory media, such as non-volatile media, include, for example, optical or magnetic disks, such as the storage device 608. Volatile media include, for example, the dynamic memory 606. Transmission media include, for example, twisted pair cables, coaxial cables, copper wire, fiber optic cables, and carrier waves that travel through space without wires or cables, such as acoustic waves, optical or electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a USB flash drive, a Blu-ray disk, a CDROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 616.

The network link 620 typically provides information communication using transmission media through one or more networks to other devices that use or process the information. For example, the network link 620 may provide a connection through the local network 622 to a host computer 624 or to ISP equipment operated by an Internet Service Provider (ISP).

A server 626, connected to the Internet, hosts a process that provides a service in response to information received over the Internet. For example, the server 626 hosts a process that provides information representing video data for presentation at the display 612. It is contemplated that the components of the computer system 600 can be deployed in various configurations within other computer systems, e.g., the host 624 and the server 626.

At least some embodiments of the invention are related to the use of the computer system 600 for implementing some or all of the techniques described herein. According to one embodiment of the invention, those techniques are performed by the computer system 600 in response to the processor 604 executing one or more sequences of one or more processor instructions contained in the memory 606. Such instructions, also called computer instructions, software and program code, may be read into the memory 606 from another computer-readable medium such as the storage device 608 or the network link 620. Execution of the sequences of instructions contained in the memory 606 causes the processor 604 to perform one or more of the method steps described herein. In alternative embodiments, hardware, such as the ASIC 616, may be used in place of or in combination with software to implement the invention. Thus, embodiments of the invention are not limited to any specific combination of hardware and software, unless otherwise explicitly stated herein.

Various forms of computer readable media may be involved in carrying one or more sequence of instructions or data or both to the processor 604 for execution. For example, instructions and data may initially be carried on a magnetic disk of a remote computer such as the host 624. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to a signal on an infra-red carrier wave serving as the network link 620. An infrared detector serving as the communication interface 618 receives the instructions and data carried in the infrared signal and places information representing the instructions and data onto the bus 602. The bus 602 carries the information to the memory 606 from which the processor 604 retrieves and executes the instructions using some of the data sent with the instructions. The instructions and data received in the memory 606 may optionally be stored on the storage device 608, either before or after execution by the processor 604.

The article presented as part of the invention is not exclusive to the description above. Other related embodiments may be derived in accordance with the principles of the invention described above. Changes within the scope of current invention may be implemented by people skilled in the art.

The exemplary embodiments of this present invention have been described in relation to systems and methods for geo-structuring. However, to avoid unnecessarily obscuring the present invention, the preceding description omits a number of known structures and devices. This omission is not to be construed as a limitation of the scope of the present invention. Specific details are set forth by use of the embodiments to provide an understanding of the present invention. It should however be appreciated that the present invention may be practiced in a variety of ways beyond the specific embodiments set forth herein.

A number of variations and modifications of the present invention can be used. It would be possible to provide for some features of the present invention without providing others.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. It is not intended to limit the present invention to the form or forms disclosed herein. In the foregoing Detailed Description, for example, various features of the present invention are grouped together in one or more embodiments, configurations, or aspects for the purpose of streamlining the disclosure. The features of the embodiments, configurations, or aspects may be combined in alternate embodiments, configurations, or aspects other than those discussed above. This method of disclosure is not to be interpreted as reflecting an intention the present invention requires more features than are expressly recited in each claim. Rather, as the following claims reflect, inventive aspects lie in less than all features of a single foregoing disclosed embodiment, configuration, or aspect.

Moreover, though the description of the present invention has included the description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Each element in the embodiments of the present disclosure may be implemented as hardware, software/program, or any combination thereof. Software codes, either in its entirety or a part thereof, may be stored in a non-transitory computer readable medium or memory (e.g., as a RAM, ROM, for example a non-volatile memory such as flash memory, CD ROM, DVD ROM, Blu-Ray™, a semiconductor ROM, USB, or a magnetic recording medium, for example a hard disk). The program may be in the form of source code, object code, a code intermediate source and object code such as partially compiled form, or in any other form.

It would be appreciated by one of ordinary skill in the art that the system and components shown in FIGS. 1-6 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims. Although the term patient and claim are utilized in the description, the terms may be used in regards to other type of records, other than medical records such as for example financial records, travel records or any personally identifiable data records and should not be limited to medical records.

What is claimed is:

1. An apparatus, comprising:
   a processor and memory configured to:
   receive data at the processor representing a plurality of clusters, wherein each cluster represents a geographic area having a centroid and a population of individuals;
   merge a first cluster having a smallest population with a second cluster having a nearest centroid based on a determination that the population of the first cluster is below a minimum size threshold to form an updated cluster that represents an updated geographic area having an updated centroid and an updated population that reflects the merging of the first cluster and the second cluster;
   re-perform the merge until each cluster meets a minimum size threshold,
   de-identify data records associated with the individuals of the clusters when the smallest cluster meets the minimum size threshold,
   assess a risk of re-identification of the de-identified clusters based on k-anonymity,
   increase the minimum size threshold and re-perform the merge, the de-identify, and the assess a risk, based on a determination that the assessed risk does not meet a risk criterion, and
   present the de-identified clusters on a display based on a determination that the assessed risk meets the risk criterion.

2. The apparatus of claim 1, wherein the processor and memory are further configured to:
   identify a smallest one of the clusters based on a number of data records of the cluster; and
   merge the smallest cluster with a second one of the clusters.

3. The apparatus of claim 2, wherein the processor and memory are further configured to:
   select the second cluster based on a geographic distance between geographic centroids of the smallest cluster and the second cluster.

4. The apparatus of claim 3, wherein the processor and memory are further configured to:
   select the second cluster based further on a socio-economic, a demographic, and/or a political parameter.

5. The apparatus of claim 1, wherein the processor and memory are further configured to:
   assess the risk of re-identification based further on optimal lattice anonymization.

6. The apparatus of claim 1, wherein the processor and memory are further configured to:
   retain a hierarchy of the merged clusters; and
   utilize the hierarchy of the merged clusters with an optimal lattice anonymization process to automatically choose a generalization scheme to provide a k-anonymous dataset with minimal suppression.

7. The apparatus of claim 1, wherein the update of the second cluster comprises calculating a new centroid based on the merged geographic areas of the first cluster and the second cluster.

8. A non-transitory computer readable medium encoded with a computer program that comprises instructions to cause a processor to:
   receive data at the processor representing a plurality of clusters, wherein each cluster represents a geographic area having a centroid and a population of individuals;
   merge a first cluster having a smallest population with a second cluster having a nearest centroid based on a determination that the population of the first cluster is below a minimum size threshold to form an updated cluster that represents an updated geographic area having an updated centroid and an updated population that reflects the merging of the first cluster and the second cluster;
   re-perform the merge until each cluster meets a minimum size threshold;
   de-identify data records associated with the individuals of the clusters when the smallest cluster meets the minimum size threshold,
   assess a risk of re-identification of the de-identified clusters based on k-anonymity;
   increase the minimum size threshold and re-perform the merge, the de-identify, and the assess a risk, based on a determination that the assessed risk does not meet a risk criterion; and
   present the de-identified clusters on a display based on a determination that the assessed risk meets the risk criterion.

9. The non-transitory computer readable medium of claim 8, further comprising instructions to cause the processor to:
   identify a smallest one of the clusters based on a number of data records of the cluster; and
   merge the smallest cluster with a second one of the clusters.

10. The non-transitory computer readable medium of claim 9, further comprising instructions to cause the processor to:
    select the second cluster based on a geographic distance between geographic centroids of the smallest cluster and the second cluster.

11. The non-transitory computer readable medium of claim 8, further comprising instructions to cause the processor to:
    select the second cluster based further on a socio-economic, a demographic, and/or a political parameter.

12. The non-transitory computer readable medium of claim 8, further comprising instructions to cause the processor to:

assess the risk of re-identification based further on optimal lattice anonymization.

13. The non-transitory computer readable medium of claim 8, further comprising instructions to cause the processor to:

retain a hierarchy of the merged clusters; and utilize the hierarchy of the merged clusters with an optimal lattice anonymization process to automatically choose a generalization scheme to provide a k-anonymous dataset with minimal suppression.

14. A computing machine implemented method, comprising:

receiving data at a processor representing a plurality of clusters, wherein each cluster represents a geographic area having a centroid and a population of individuals;

merging a first cluster having a smallest population with a second cluster having a nearest centroid based on a determination that the population of the first cluster is below a minimum size threshold to form an updated cluster that represents an updated geographic area having an updated centroid and an updated population that reflects the merging of the first cluster and the second cluster;

repeating the merging until each cluster meets a minimum size threshold;

de-identifying data records associated with the individuals of the clusters when the smallest cluster meets the minimum size threshold;

assessing a risk of re-identification of the de-identified clusters based on k-anonymity;

increasing the minimum size threshold and repeating the merging, the de-identifying, and the assessing a risk, based on a determination that the assessed risk does not meet a risk criterion; and presenting the de-identified clusters on a display based on a determination that the assessed risk meets the risk criterion.

15. The computing machine implemented method of claim 14, wherein the merging comprises:

identifying a smallest one of the clusters based on a number of data records of the cluster; and merging the smallest cluster with a second one of the clusters.

16. The computing machine implemented method of claim 15, wherein the merging further comprises:

selecting the second cluster based on a geographic distance between geographic centroids of the smallest cluster and the second cluster.

17. The computing machine implemented method of claim 16, wherein the selecting comprises:

selecting the second cluster based further on a socio-economic, a demographic, and/or a political parameter.

18. The computing machine implemented method of claim 14, wherein the assessing comprises:

assessing the risk of re-identification based further on optimal lattice anonymization.

19. The computing machine implemented method of claim 14, further comprising:

retaining a hierarchy of the merged clusters; and utilizing the hierarchy of the merged clusters with an optimal lattice anonymization process to automatically choose a generalization scheme to provide a k-anonymous dataset with minimal suppression.

* * * * *